(12) United States Patent
Endo et al.

(10) Patent No.: US 6,270,899 B1
(45) Date of Patent: Aug. 7, 2001

(54) ESTER COMPOUND AND THERMOSETTING RESIN COMPOSITION USING THE SAME

(75) Inventors: Yasuhiro Endo; Toshiaki Hayashi, both of Tsukuba (JP)

(73) Assignee: Sumitomo Chemical Company, Limited (JP)

( * ) Notice: Subject to any disclaimer, the term of this patent is extended or adjusted under 35 U.S.C. 154(b) by 0 days.

(21) Appl. No.: 08/870,009

(22) Filed: Jun. 6, 1997

(30) Foreign Application Priority Data

Jun. 6, 1996 (JP) .................................................. 8-144446
Aug. 30, 1996 (JP) .................................................. 8-230554

(51) Int. Cl.$^7$ .......................... B32B 27/38; B32B 15/08; C08L 61/06; C08G 8/02
(52) U.S. Cl. .......................... 428/413; 428/418; 525/481; 525/508; 528/128; 528/155
(58) Field of Search ..................... 428/413, 418, 428/416; 525/481, 508; 528/128, 155

(56) References Cited

U.S. PATENT DOCUMENTS

| | | | |
|---|---|---|---|
| 2,418,459 | * 4/1947 | Bousquet | 167/33 |
| 2,904,531 | * 9/1959 | Bruin et al. | 260/47 |
| 3,650,799 | * 3/1972 | Young, Jr. et al. | 117/33.3 |
| 4,297,457 | * 10/1981 | Stark, Jr. | 525/507 |
| 4,334,067 | * 6/1982 | Ohno et al. | 544/151 |
| 4,387,207 | * 6/1983 | Edwards | 528/86 |
| 5,182,184 | * 1/1993 | Lazarus et al. | 430/165 |
| 5,283,324 | * 2/1994 | Tomiaka et al. | 534/557 |
| 5,290,657 | * 3/1994 | Uetani et al. | 430/191 |
| 5,374,742 | * 12/1994 | Uetani et al. | 549/223 |
| 5,436,107 | * 7/1995 | Tomiaka et al. | 430/192 |
| 5,478,871 | * 12/1995 | Takebe et al. | 523/443 |
| 5,556,995 | * 9/1996 | Suzuki et al. | 549/406 |
| 5,587,492 | * 12/1996 | Tomioka et al. | 549/406 |
| 5,644,003 | * 7/1997 | Arai et al. | 525/423 |
| 5,726,257 | * 3/1998 | Ueda et al. | 525/508 |

FOREIGN PATENT DOCUMENTS

| | | |
|---|---|---|
| 598320 | * 5/1994 | (EP) . |
| 699 670 | 3/1996 | (EP) . |
| 709 736 | 5/1996 | (EP) . |
| 814694 | 6/1959 | (GB) . |
| 62-53327 | * 3/1987 | (JP) . |
| 8-99931 | * 4/1996 | (JP) . |
| 8-169937 | * 7/1996 | (JP) . |
| 8-269039 | * 10/1996 | (JP) . |

OTHER PUBLICATIONS

Chemical Abstracts, Epoxy Resin Compositions for Copper Clad Laminates, vol. 125, No. 16, 1996, Yamazaki et al., p. 88.

\* cited by examiner

Primary Examiner—D. S. Nakarani
Assistant Examiner—Holly C. Rickman
(74) Attorney, Agent, or Firm—Fitch, Even, Tabin & Flannery

(57) ABSTRACT

An ester compound prepared by esterifying at least one OH group of a polyhydric phenol as a condensation product of a non-substituted or substituted resorcinol and a carbonyl compound with an organic carboxylic acid having 1 to 20 carbon atoms or a derivative thereof, which necessarily contain an organic carboxylic polyacid having 1 to 20 carbon atoms or a derivative thereof. The ester compound can be used as an epoxy resin curing agent affording a cured article having low dielectric constant, low moisture absorption and sufficient heat resistance.

9 Claims, No Drawings

ESTER COMPOUND AND THERMOSETTING RESIN COMPOSITION USING THE SAME

BACKGROUND OF THE INVENTION

1. Field of the Invention

The present invention relates to an ester compound which can mainly be used as an epoxy resin curing agent affording a cured article having low dielectric constant, low moisture absorption and sufficient heat resistance, and an epoxy resin composition using the same. The ester compound and epoxy resin composition are particularly suitable for electric/electronic applications to cope with high frequency, such as resin for laminate, resin for sealing IC, etc., and are also used as molding materials, coating materials, adhesive materials, civil engineering and construction materials and the like.

2. Description of the Related Art

As materials for printed circuit board among epoxy resins used for electric/electronic applications, a combination of a bisphenol type epoxy resin and dicyandiamide has mainly been used, heretofore. With the recent realization of thin volume and multi-layer construction of the printed circuit board, low dielectric constant of the resin is required for the purpose of improving a signal velocity and impedance-matching of a circuit. Also, with the recent realization of high frequency of the signal, low dielectric dissipation factor of the resin for the purpose of reducing transmission loss of the signal is required.

A method of using a conventional epoxy resin in combination with a thermoplastic resin having low dielectric constant and low dielectric dissipation factor is suggested. Examples thereof include method of modifying with a reactive polybutadiene resin, method of dispersing powders of a polytetrafluoroethylene resin and the like.

Recently, transfer molding of an epoxy resin composition, which is economically useful, has been conducted for sealing semiconductors such as LSI, IC, transistor and the like. Particularly, surface-mounted packaging of LSI is conducted and there has been increased a case where LSI is directly immersed in a solder bath. In that case, since the resin-sealed package is exposed to high temperature of not less than 200° C., water adsorbed in the resin-sealed package expands to cause a problem that a crack is formed in a sealing package for semiconductor.

Therefore, an improvement in low moisture absorption and low crack resistance is required to an epoxy resin sealing material. At present, glycidyl ether of o-cresol novolak is mainly used as the epoxy resin and a sealing material containing phenol novolak is mainly used as a curing agent. However, the above problems arise when the resin-sealed package absorbs moisture during the preservation so that it is practically used after moisture-proof packaging to avoid the problems. In order to solve these problems, a low-viscosity epoxy resin capable of charging a filler in high density, e.g. glycidyl ether epoxy resin having a tetramethylbiphenyl skeleton, have been developed for the purpose of obtaining low water absorption and is practically used. An epoxy resin wherein the moisture resistance is obtained by having a hydrophobic skeleton of dicyclopentadiene-phenol addition polymer, alkylene phenol, etc. is also developed.

However, these conventional techniques have the following problem. That is, the proportion of a thermoplastic resin to be used in combination becomes large so as to accomplish the desired dielectric constant because the dielectric constant of the epoxy resin as the base of the material for printed circuit board is high. Therefore, the heat resistance, adhesion properties, dimensional stability, chemical resistance, etc., as a feature of the epoxy resin, are deteriorated.

A current resin for sealing material, e.g. sealing material containing glycidyl ether of o-cresol novolak as a main component, is well-balanced in view of the heat resistance and moldability, but is inferior to a biphenyl type epoxy as a sealing resin for surface-mounted packaging. The biphenyl type epoxy has low moisture absorption and shows excellent physical properties as the sealing material for surface packaging. However, the heat resistance is inferior and a package crack is formed under high moisture absorption condition and, therefore, physical properties thereof are still to be insufficient. In case of an epoxy having a hydrophobic skeleton, there is a problem that the heat resistance is inferior because a distance between crosslinking points becomes long.

Therefore, desired now are an epoxy resin curing agent capable of producing a cured article having low dielectric constant, low dielectric dissipation factor and low moisture absorption without deteriorating the heat resistance, adhesion properties and workability of a conventional epoxy resin, and a composition thereof.

SUMMARY OF THE INVENTION

The present inventors have intensively studied about a functional group structure and a skeletal structure of the compound capable of thermosetting with the epoxy resin. As a result, it has been found that an epoxy resin composition using the compound having a specific functional group structure and a specific skeletal structure satisfies the above object. Thus, the present invention has been completed.

That is, the present invention relates to an ester compound prepared by esterifying at least one OH group of a polyhydric phenol which is a condensation product of a non-substituted or substituted resorcinol represented by the following general formula (1):

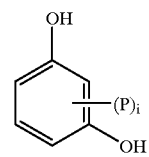

(1)

(wherein P independently represent a halogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms; and i represents an integer of 0 to 2> and a carbonyl compound represented by the following general formula (2):

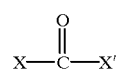

(2)

(wherein x and x' independently represent a hydrogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms, and x and x' may form a ring) with an organic carboxylic acid having 1 to 20 carbon atoms or a derivative thereof, which necessarily contain an organic carboxylic polyacid having 1 to 20 carbon atoms or a derivative thereof;

a method for producing the ester compound, which comprises esterifying a product, obtained by condensing the compound represented by the general formula (1) with the compound represented by the general formula (2) in the presence of an acid catalyst, with an organic carboxylic acid having 1 to 20 carbon atoms or a derivative thereof, which necessarily contain an organic carboxylic polyacid having 1 to 20 carbon atoms or a derivative thereof, in the presence of a base; an epoxy resin composition comprising:

(A) an epoxy resin, and (B) the above ester compound as an essential component; a copper-clad laminate and a build-up laminate, obtained by using the above composition; and a resin-sealed type semiconductor device.

More preferred one as the ester compound of the present invention is an ester compound wherein a polyhydric phenol as a raw material is represented by the following general formula (3)

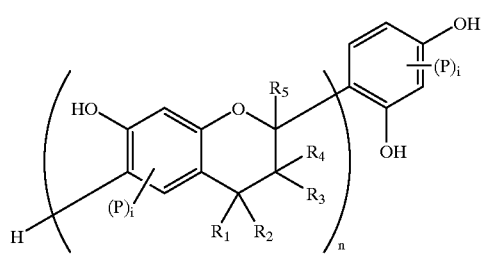

(3)

(wherein n represents an average repeating number and is from 1 to 20; P independently represent a halogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms; i represents an integer of 0 to 2; and R1, R2, R3, R4 and R5 independently represent a hydrogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms, and R1 and R2 as well as R4 and R5 may respectively form a ring).

An equivalent ratio of the whole organic carboxylic acids used for synthesizing an ester to the polyhydric phenol as the raw material is preferably not less than 30 equivalent %, more preferably not less than 50 equivalent %.

A proportion of the organic carboxylic polyacid having 1 to 20 carbon atoms or a derivative thereof is within the range from 10 to 50 equivalent %, based on the organic carboxylic acid having 1 to 20 carbon atoms or a derivative thereof used for esterification. When the proportion is less than the above range, the heat resistance of the cured article of a thermoplastic resin composition is lowered. On the other hand, when the proportion is more than the above range, the molecular weight becomes high at the time of synthesizing an ester, which leads to gelation.

In the general formula (3), n represents an average repeating number and can take the value of 1 to 20. The value is preferably from 1 to 10 in view of the operatability.

The polyhydric phenol compound as the raw material of the ester compound of the present invention can be obtained by a known method such as condensation reaction between resorcinols and a carbonyl compound in the presence of an acid.

The resorcinols are those having no substituent at the 4- and the 6-positions, and examples thereof include alkylresorcinols such as resorcinol, 2-methylresorcinol, 5-methylresorcinol, 2-propylresorcinol, 2-n-butylresorcinol, 5-isobutylresorcinol, 5-t-butylresorcinol, 5-octylresorcinol, 5-nonylresorcinol, 2,5-dimethylresorcinol, 2,5-diethylresorcinol, 2,5-diisopropylresorcinol, 2-methyl-5-butylresorcinol, 2-methyl-5-nonylresorcinol, etc.; cycloalkylresorcinols such as 2-cyclopentyl resorcinol, 2-cyclohexylresorcinol, 2-cycloheptylresorcinol, etc.; arylresorcinols such as 5-phenylresorcinol, 5-naphthylresorcinol, etc.; aralkylresorcinols such as 5-benzylresorcinol, 5-phenethylresorcinol, etc.; or halogenated resorcinols such as 2-chlororesorcinol, 5-chlororesorcinol, 2,5-dichlororesorcinol, 2-bromoresorcinol, 5-bromoresorcinol, 2,5-dibromoresorcinol, 2-iodoresorcinol, 5-iodoresorcinol, 2,5-diiodoresorcinol, etc.

Examples of the carbonyl compound include aldehydes such as formaldehyde, acetaldehyde, propionaldehyde, butyladehyde, pentylaldehyde, phenylacetaldehyde, cyclohexylacetaldehyde, etc.; and ketones such as acetone, methyl ethyl ketone, diethyl ketone, methyl propyl ketone, methyl isobutyl ketone, cyclohexanone, methyl cyclohexanone, cycloheptanone, benzyl phenyl ketone, benzyl methyl ketone, methyl phenethyl ketone, acetophenone, acetonaphthenone, indan-1-on, etc.

Examples of the acid catalyst used for the condensation reaction between the resorcinols and carbonyl compound include inorganic acid such as hydrochloric acid, sulfuric acid, etc.; organic acid such as p-toluenesulfonic acid, benzenzesulfonic acid, methanesulfonic acid, etc.; and solid acid and acid ion-exchange resin, such as acid clay, active alumina, zeolite, etc. These acid catalysts are used in an amount of 0.01 to 50% by weight, more preferably from 0.5 to 20% by weight, based on the total weight of the resorcinols and carbonyl compound to be charged as the raw material.

In the condensation reaction, a known non-reactive organic solvent may be used, and examples thereof include toluene, xylene, dioxane, tetrahydrofuran, N,N-dimethylformamide, N,N-dimethylacetamide, N-methyl-2-pyrrolidone, methanol, ethanol, etc., but are not limited thereto.

In case of the condensation reaction, a molar ratio of the resorcinols to the carbonyl compounds is preferably from 0.1 to 20, more preferably from 0.3 to 1.5. When the molar ratio exceeds this range, there arouse a problem that residue of excess resorcinol or an OH residue of the product becomes small. The reaction temperature is preferably from 0 to 200° C., more preferably from 20 to 160° C. When the reaction temperature exceeds this range, the conversion rate is lowered when the temperature is low. On the other hand, when the temperature is high, a large amount of by-products is produced. The reaction time is preferably from 1 to 100 hours, more preferably from 2 to 80 hours. When the reaction time exceeds this range, the reaction becomes insufficient when the reaction times is short. Even if the reaction time is longer than this range, the yield does not change and, therefore, it is not economical.

In case of the condensation reaction, water produced during the reaction may be removed from the system or not. In case of removing water, the reaction may be conducted with a solvent capable of azeotropic dehydration, such as toluene, xylene, etc., using a device capable of reacting with removing water in the system, such as Dean-Stark tube. The reaction may be conducted under reduced pressure to accelerate dehydration.

The esterification of the condensation reaction product is conducted by reacting with an organic carboxylic acid having 1 to 20 carbon atoms, or an acid anhydride or acid halide thereof in the presence of a base.

The organic carboxylic acid and a derivative thereof are exemplified as follows.

The organic carboxylic polyacid which is essential in the synthesis of the ester of the present invention, and a derivative thereof represent an organic carboxylic compound having two or more carboxyl groups, and an acid anhydride or acid halide thereof. Examples thereof include aliphatic polycarboxylic acid (e.g. oxalic acid, malonic acid, succinic acid, adipic acid, azelaic acid, maleic acid, fumaric acid, citraconic acid, etc.) and an acid halide or acid anhydride thereof; aromatic polycarboxylic acid (e.g. phthalic acid, isophthalic acid, terephthalic acid, naphthalenedicarboxylic acid, benzenetricarboxylic acid, etc.) and an acid halide or acid anhydride thereof; and alicyclic polycarboxylic acid (e.g. cyclopentanedicarboxylic acid, cyclohexanedicarboxylic acid, cycloheptanedicarboxylic acid, etc.) and an acid halide or acid anhydride thereof. Among them, malonic acid, succinic acid, adipic acid, maleic acid, fumaric acid, isophthalic acid, terephthalic acid, naphthalenedicarboxylic acid and cyclohexanedicarboxylic acid, and an acid halide or acid anhydride thereof are preferred.

Examples of the organic carboxylic acid other than the polyacid which can be used for synthesizing the ester of the present invention, or a derivative thereof include aliphatic monocarboxylic acid (e.g. formic acid, acetic acid, propionic acid, butyric acid, valeric acid, lauric acid, stearic acid, phenylacetic acid, bromoacetic acid, acrylic acid, methacrylic acid, etc.) and an acid halide or acid anhydride thereof; aromatic monocarboxylic acid (e.g. benzoic acid, methylbenzoic acid, napthoic acid biphenylcarboxylic acid, etc.) and an acid halide or acid anhydride thereof; and alicyclic monocarboxylic acid (e.g. cyclopentanecarboxylic acid, cyclohexanecarboxylic acid, cycloheptanecarboxylic acid, etc.) and an acid halide or acid anhydride thereof. Among them, acetic acid, propionic acid, methacrylic acid and benzoic acid, and an acid halide or acid anhydride thereof are preferred.

Examples of the basic compound used in the esterification reaction include inorganic base compound such as sodium hydroxide, potassium hydroxide, etc.; and organic base compound such as pyridine, triethylamine, tripheylamine, imadazole compound.

In the esterification reaction, a known solvent may be used. Examples thereof include tolune, xylene, acetone, methyl ethyl ketone, methyl isobutyl ketone, cyclohexanone, dioxane, tetrahydrofuran, N,N-dimethylformamide, N,N-dimethylacetamide, N-methyl-2-pyrrolidone and the like. Among them, tolune, xylene and methyl isobutyl ketone are preferred.

A molar equivalent ratio of the whole organic carboxylic acids or a derivative thereof used in case of the esterification reaction to the OH group of the polyhydric phenol is preferably from 0.3 to 2.0, more preferably from 0.5 to 1.5. When the molar equivalent ratio exceeds this range, there arouse a problem that residue or excess resorcinol or an OH residue of the product becomes small. The reaction temperature is preferably from 20 to 200° C., more preferably from 40 to 150° C. When the reaction temperature exceeds this range, the conversion rate is lowered when the temperature is low. When the temperature is high, a large amount of by products is produced. The reaction time is preferably from 2 to 50 hours, more preferably from 4 to 30 hours. When the reaction time exceeds this range, the reaction becomes insufficient when the reaction times is short. Even if the reaction time is longer than this range, the yield does not change and, therefore, it is not economical.

When using the organic carboxylic acid itself as the raw material in case of the esterification reaction, water produced during the reaction may be removed from the system or not. In case of removing water, the reaction may be conducted with a solvent capable of azeotropic dehydration, such as toluene, xylene, methyl isobutyl ketone, etc., using a device capable of reacting with removing water in the system, such as Dean-Stark tube. The reaction may be conducted under reduced pressure to accelerate dehydration.

The epoxy resin used in the present invention is a known compound containing two or more epoxy groups in the molecule, and a chemical structure thereof is not specifically limited. Examples thereof include difunctional epoxy such as diglycidyl ether of bisphenol A, diglycidyl ether of tetrabromobisphenol A, etc.; trifunctional epoxy such as glycidyl ether of tris(4-hydroxyphenyl)methane, glycidyl ether of 1,1,1-tris(4-hydroxyphenyl)ethane, etc.; polyfunctional epoxy such as glycidyl ether of phenol novolak, glycidyl ether of cresol novolak, glycidyl ether of novolak obtained by water-eliminating condensation of phenols and hydroxyarylaldehydes, glycidyl ether of poly(hydroxystyrene), glycidyl ether of phenol-modified polybutadiene, glycidyl ether of phenol-dicyclopentadiene adduct, glycidyl ether of bisphenol A novolak, etc.; product obtained by previously reacting an epoxy resin with a phenol compound such as bisphenol A, resorcinol, tetrabromobisphenol A, etc.; and a mixture of two or more epoxy resins. Examples of those used for affording preferable results with respect to the object of the present invention include glycidyl ether of novolak of 2-t-butyl-5-methylphenol, glycidyl ether of cyclohexylphenolnovolak, glycidyl ether of octylphenol novolak, diglycidyl ether of 1,1-(4-hydroxy-5-t-butyl-2-methylphenyl)butane, diglycidyl ether of limonenebis(2-sec-butylphenol), glycidyl ether of tris(4-hydroxyphenyl)methane, glycidyl ether of 1,1,1-tris(4-hydroxyphenyl), glycidyl ether of phenol novolak, glycidyl ether of cresol novolak, glycidyl ether of novolak obtained by water-eliminating condensation of phenols and hydroxyarylaldehydes, glycidyl ether of phenol-dicyclopentadiene adduct, glycidyl ether of bisphenol A novolak and the like.

A proportion of the epoxy resin to the ester compound is adjusted so that a molar ratio of the number of moles of the epoxy group in the epoxy resin to those of the ester group in the ester compound is preferably from 1.0:0.3 to 1.0:1.5, more preferably from 1.0:0.5 to 1.0:1.2. When the molar ratio is out of this range, curing failure arises and a good cured article is not obtained.

A curing accelerator may be added to the epoxy resin composition of the present invention. Examples thereof include imidazoles such as 2-ethyl-4-methylimidazole, etc.; tertiary amines such as triethylamine, benzyldimethylamine, 1,4-diazabicyclo[2.2.2]octane, 1,8-diazabicyclo[5.4.0]-7-undecene, etc.; quaternary ammonium salts such as terta-n-butyl ammonium bromide, terta-n-butyl ammonium chloride, tetra n-amylammonium bromide, etc.; and phosphorous compounds such as triphenylphosphine, etc. The curing accelerator is preferably added so that the amount is from 0.05 to 10% by weight, based on the whole resin.

It is also possible to use a thermoplastic resin, or a thermosetting resin other than the epoxy resin, so far as the effect of the present invention is not damaged. Specific examples thereof include thermoplastic resin such as polyethylene, polypropylene, polybutadiene, polystyrene, methyl polymethacrylate, polyvinyl chloride, polyvinyl acetate, polycellulose, polyamide, polyimide, silicone resin, polybenzimidazole, polyimide amide, polyquinoline, polyacetal, polycarbonate, polyester, polyphenylene oxide, polysulfone, fluorinated resin, natural rubber or polyisoprene, or a mixture thereof; thermosetting resin such as phenol resin, urea resin, melamine resin, xylene resin, diallyl phthalate resin, unsaturated polyester, saturated alkyd resin, cyanate resin, maleimide resin, vinylbenzyl resin, aniline resin, furan resin, polyurethane, alkylbenzene resin or guanamine resin, or a mixture thereof; or a mixture of these thermoplastic resins and thermosetting resins.

Known additives such as flame retardants, fillers, surface-treating agents, etc. may be added to the composition of the present invention for each purpose.

The flame retardant may be an organic or inorganic compound, and known flame retardants can be optionally used. Among them, glycidyl ether of tetrabromobisphenol A and glycidyl ether of bromo-containing phenol novolak are preferred in view of good availability, but the flame retardant is not limited thereto.

These flame retardants can be formulated in the resin composition in any proportion, and are added to such a degree that the UL standard V-O as an instruction of flame retardance can be accomplished. When the flame retardant is added in the among larger than that to be required, characteristics such as Tg, dielectric constant, etc. are damaged.

The production of the laminate of the present invention can be conducted using a normal method. Examples of the general method for production include method of impregnating a base material with a resin varnish as a solution, prepared by dissolving a thermosetting resin composition in an organic solvent, heat-treating the base material to form a prepreg; laminating the prepreg and a copper foil each other, followed by thermoforming to obtain a copper-clad laminate, build-up method of building-up each conductive layer on a base material as a base using a prepreg or a copper foil coated with a resin with plating to form a multi-layer printed circuit board, but are not limited thereto.

Examples of the organic solvent used include acetone, methyl ethyl ketone, methyl isobutyl ketone, ethylene glycol monomethyl ether, propylene glycol dimethyl ether, propylene glycol monomethyl ethyl, toluene, xylene, 1,4-dioxane, tetrahydrofuran, N,N-dimethylformamide, or a mixture thereof.

Examples of the base material to be impregnated with the resin varnish include woven fabric of inorganic or organic fibers such as glass fibers, alumina fibers, polyester fibers, polyamide fibers, etc., nonwoven fabric, mat, paper or a combination thereof.

Although the heat treatment condition of the prepreg is appropriately selected according to the kind and amount of the solvent, catalyst and other various additives used, the heat treatment is normally conducted at the temperature of 100 to 200° C. for 3 minutes to 30 minutes.

Examples of the laminating/thermoforming method of the prepreg and copper foil include method of hot-press molding at the temperature of 150 to 300° C. under the molding pressure of 10 to 100 kg/cm$^2$ for 20 to 300 minutes.

Examples of the inorganic filler as the component (C) in the epoxy resin composition include silica, alumina, titanium white, aluminum hydroxide, talc, clay, glass fibers and the like. Among them, silica and alumina are particularly preferred. It is also possible to use those which are different in shape (spherical or crushed type) or size in combination to increase the amount charged. It is necessary that the amount of the inorganic filler formulated is from 25 to 97% by weight, preferably from 40 to 90% by weight, based on the total amount of the resin composition.

It is preferred that the fillers used in the present invention are sufficiently mixed in advance. Specifically, it is possible to mix them using a device of utilizing a rotating blade or air (e.g. mixer, Ko-kneader, etc.) or a device of vibrating, shaking or rotating. In order to judge whether the fillers are sufficiently kneaded or not, a particle size distribution of samples at different position may be measured to examine whether they are substantially the same or not. The fillers may be optionally treated with a coupling agent or a resin in advance. Examples of the treating method include method of mixing with a solvent and distilling off the solvent and method of directly formulating it in the fillers, followed by treating using a mixer.

In the present invention, there may optionally be used natural wax, synthetic wax, higher fatty acid and metal salts, releasing agent (e.g. paraffin, etc.), colorant (e.g. carbon black, etc.) and surface-treating agent (e.g. silane coupling agent, etc.). Flame retardants such as antimony trioxide, phosphorous compound, brominated epoxy resin, etc. A brominated epoxy resin is particularly preferred to impart a flame retardant effect.

In order to realize low stress, various elastomers may be added or reacted previously. Specific examples thereof include addition type or reaction type elastomer, such as polybutadiene, butadiene-acrylonitrile copolymer, silicone rubber, silicone oil and the like.

In order to produce a resin-sealed type semiconductor device by sealing electronic parts such as semiconductor, etc. using the resin composition of the present invention, cure molding may be conducted by a molding method which has hitherto been known, such as transfer molding, compression molding, injection molding, pot molding, dipping, fluidization dipping and the like.

PREFERRED EMBODIMENT OF THE INVENTION

The following Examples further illustrate the present invention in detail but are not to be construed to limit the scope thereof. In the Examples, the "epoxy equivalent" is defined by a molecular weight of an epoxy resin per one epoxy group, and the "OH equivalent" is defined by a molecular weight of a polyphenol compound per one OH group.

SYNTHESIS EXAMPLE 1

This Synthesis Example relates to a method of producing glycidyl ether of 2-t-butyl-5-methylphenol novolak, as the epoxy resin used for the epoxy resin composition of the present invention.

2-t-butyl-5-methylphenol (2231.0 g, 13.58 OH mol eq.), p-toluenesulfonic acid (12.9 g, 0.068 mol) and deionized water (223.3 g) were charged in a 5 liter four-necked round bottom flask equipped with a thermometer, a stirrer, a condenser and a dropping tube, followed by heating to 100° C. After 37% formalin (218.4 g, 2.715 mol) was added dropwise over 2 hours, the reaction was conducted with maintaining at 100° C. for 2 hours. After cooling to 80° C., the reaction solution was neutralized with an aqueous 10% NaOH solution (27.7 g, 0.069 mol). The organic layer after partitioning was washed twice with 700 g of deionized water. The organic layer after washing was concentrated under reduced pressure (180° C., 10 mmHg, 1 hour) to obtain 857.2 g of a resinous product. The OH equivalent of the resulting resinous product was 176.0 g/eq.

The reaction product (246.4 g, 1.4 OH mol eq.) obtained as described above, epichlorohydrin (906.5 g, 9.8 mol), dimethylsulfoxide (453.3 g) and deionized water (14.0 g) were charged in a 2 liter four-necked round bottom flask equipped with a thermometer, a stirrer and a condenser with a separating tube, and then an aqueous 48.6% sodium hydroxide solution (108.31 g, 1.316 mol) was added dropwise over 5 hours under the condition of 49° C. and 42 torr. During the dropwise addition, azeotropically distilling epichlorohydrin and water were liquefied by cooling with maintaining at 49° C. and the reaction was conducted with returning the organic layer to the reaction system.

After the completion of the reaction, the unreacted epichlorohydrin was removed by concentrating under reduced pressure. Then, an epoxidated product containing a salt as by-products and dimethylsulfoxide was dissolved in methyl isobutyl ketone and the salt and dimethylsulfoxide were removed by washing with hot water. 304.9 g of an epoxy resin was obtained by removing the solvent under reduced pressure.

The epoxy equivalent of the epoxy resin thus obtained was 256 g/eq. An infrared absorption spectrum was measured. As a result, it was confirmed that absorption at 3200–3600 cm–1 of phenolic OH is disappeared and absorption at 1240 and 910 cm–1 of epoxide is present.

SYNTHESIS EXAMPLE 2

This Synthesis Example relates to a method of producing a terminal epoxy resin by addition reaction of the epoxy resin obtained in Synthesis Example 1, diglycidyl ether of tetrabromobisphenol A and tetrabromobisphenol A.

The epoxy resin (83.8 g) obtained in Synthesis Example 1, diglycidyl ether of tetrabromobisphenol A (trade name: Sumi-epoxy ESB-400 manufactured by Sumitomo Chemical Co., Ltd., epoxy equivalent: 403 g/eq.) (75.5 g), tetrabromobisphenol A (17.5 g) and methyl ethyl ketone (15.9 g) were charged in a 300 ml four-necked round bottom flask equipped with a thermometer, a condenser and a stirrer, followed by melting with heating at 110° C. A 10% methyl ethyl ketone solution of triphenylphosphine (weight ratio of triphenylphosphine to resin:4×10–4) (0.71 g) was added and, after maintaining at 110° C. for 4 hours, the addition reaction of the epoxy group and phenolic hydroxyl group was conducted. After the completion of the reaction, the inside of the system was cooled to 90° C. and 63.5 g of propylene glycol monomethyl ether was added dropwise to obtain 250 g of a resin solution having a resin solid content of 70% by weight. The epoxy equivalent of the resulting resin adduct was 390.0 g/eq. in terms of solid content.

SYNTHESIS EXAMPLE 3

This Synthesis Example relates to a method of producing glycidyl ether of a polyhydric phenol obtained by the reaction between 2-t-butyl-5-methylphenol and p-hydroxybenzaldehyde, as the epoxy resin used for the epoxy resin composition of the present invention.

2-t-butyl-5-methylphenol (295.6 g, 1.80 OH mol eq.), p-toluenesulfonic acid (0.95 g, 0.05 mol), p-hydroxybenzaldehyde (122.1 g, 1.00 ml) and toluene (417.7 g) were charged in a reaction flask equipped with a thermometer, a stirrer, a condenser and a Dean-Stark tube, and the condensation reaction was conducted at reflux with dehydrating at 115° C. for 5 hours. After cooling to 70° C., the reaction solution was neutralized with sodium hydroxide. Hexane (417.7 g) was added to form a precipitate again. After cooling to room temperature, the solvent was filtered and dried under reduced pressure to obtain 372 g of a polyhydric phenol. The OH equivalent was 140 g/eq.

The polyhydric phenol (294.0 g, 2.1 OH mol eq.) obtained as described above, epichlorohydrin (971.6 g, 10.5 mol) and dimethylsulfoxide (245.6 g) were charged in a reaction flask equipped with a thermometer, a stirrer and a condenser with a separating tube, and then an aqueous 48% sodium hydroxide solution (164.5 g, 1.974 mol) was added dropwise over 5 hours under the conditions of 48° C. and 62 torr. During the dropwise addition, azeotropically distilling epichlorohydrin and water were liquefied by cooling with maintaining at 48° C. and the reaction was conducted with returning the organic layer to the reaction system.

After the completion of the reaction, the unreacted epochlorohydrin was removed by concentrating under reduced pressure. Then, an epoxidated product containing a salt as by-products and dimethylsulfoxide was dissolved in methyl isobutyl ketone and the salt and dimethylsulfoxide were removed by washing with hot water. 380 g of an epoxy resin was obtained by removing the solvent under reduced pressure.

The epoxy equivalent of the epoxy resin thus obtained was 210 g/eq.

SYNTHESIS EXAMPLE 4

This Synthesis Example relates to a method of producing a polyhydric phenol, 2,4,4-trimethyl-2-(2,4-dihydroxyphenyl)-7-hydroxychroman (CAS No. 26505-28-2) as the raw material of the ester compound of the present invention.

Resorcinol (1000.0 g, 9.1 mol), p-toluenesulfonic acid (6.9 g, 0.036 mol), methanol (330.0 g) and acetone (176.0 g, 3.0 ml) were charged in a 5 liter four-necked round bottom flask equipped with a thermometer, a stirrer, a condenser and a dropping funnel, followed by heating to 65° C. After maintaining at 65° C. for 9 hours, 750 g of deionized water was charged. After maintaining at 40° C. for 3 hours, the deposited crystal was filtered and washed. The resulting crude crystal was dissolved in methanol, and deionized water was added dropwise, followed by recrystallization. An amount of the product obtained after filtration and further drying under reduced pressure was 265 g. It was confirmed by $^1$H-NMR and IR that the resultant is an desired product.

EXAMPLE 1

This Example relates to a method of producing the ester of the present invention, wherein a molar equivalent ratio of a dicarboxylic acid derivative (terephthaloyl dichloride) to a monocarboxylic acid derivative (acetic anhydride) is 30%.

2,4,4-Trimethyl-2-(2,4-dihydroxyphenyl)-7-hydroxychroman (70 g, 0.7 mol eq.) obtained in Synthesis Example 4, triethylamine (77.8 g, 0.77 mol eq.) and methyl isobuthyl ketone (300.8 g) are charged in a 2 liter four-necked flask equipped with a condenser, a thermometer, a stirrer and a dropping funnel, followed by heating to 70° C. After adding dropwise a slurry solution prepared by dissolving terephthaloyl dichloride (21.3 g, 0.21 mol eq.) in 168.0 g of methyl isobuthyl ketone, acetic anhydride (57.1 g, 0.56 mol eq.) is added dropwise over one hour. After heating to 90° C. and maintaining for 5 hours, a salt was removed by washing with water and the solvent was removed under reduced pressure to obtain 96.9 g of a resinous solid.

Infrared absorption spectrum: 2970, 1760 (carbonyl stretching of acetate), 1740 (carbonyl stretching of terephthalate), 1605, 1580, 1490, 1410, 1365, 1240, 1200, 1145, 1120, 1100, 1070, 1055, 1010, 900, 720 cm–1

Absorption due to OH stretching vibration was not observed.

EXAMPLE 2

This Example relates to a method of producing the ester of the present invention, wherein a molar equivalent ratio of a dicarboxylic acid derivative (terephthaloyl dichloride) to a monocarboxylic acid derivative (acetic anhydride) is 30%.

2,4,4-Trimethyl-2-(2,4-dihydroxyphenyl)-7-hydroxychroman (150 g, 1.5 mol eq.) obtained in Synthesis Example 4 and METHYL ISOBUTHYL KETONE (858 g) are charged in a 2 liter four-necked flask equipped with a condenser, a thermometer, a stirrer and a dropping funnel, and then dissolved by heating to 50° C. After charging dichloride terephthalate (45.7 g, 0.45 mol eq.), triethylamine (45.5 g, 0.45 mol) is added dropwise over one hour. Triethylamine (121.2 g, 1.2 mol) is charged and, after heating to 70° C., acetic anhydride (122.4 g, 1.2 mol eq.) is added dropwise over one hour. After heating to 90° C. and maintaining for 4 hours, a slat was removed by washing with water and the solvent was removed under reduced pressure to obtain 215.2 g of a resinous solid.

According to the same manner as that described in Example 1. it was confirmed that the resultant is a desired product.

EXAMPLE 3

This Example relates to a method of producing the ester of the present invention, wherein a molar equivalent ratio of a dicarboxylic acid derivative (terephthaloyl dichloride) to a monocarboxylic acid derivative (acetic anhydride) is 20%.

2,4,4-Trimethyl-2-(2,4-dihydroxyphenyl)-7-hydroxychroman (150 g, 1.5 mol eq.) obtained in Synthesis Example 4 and METHYL ISOBUTHYL KETONE (880 g) are charged in a 2 liter four-necked flask equipped with a condenser, a thermometer, a stirrer and a dropping funnel, and then dissolved by heating to 50° C. After charging terephthaloyl dichloride (30.5 g, 1.5 mol eq.), triethylamine (30.3 g, 0.3 mol) is added dropwise over one hour. Triethylamine (136.4 g, 1.35 mol) is charged and, after heating to 70° C., acetic anhydride (137.7 g, 1.35 mol eq.) is added dropwise over one hour. After heating to 90° C. and maintaining for 5 hours, a salt was removed by washing with water and the solvent was removed under reduced pressure to obtain 217.9 g of a resinous solid having a softening point of 101° C.

According to the same manner as that described in Example 1. it was confirmed that the resultant is a desired product.

EXAMPLE 4

This Example relates to a method of producing the ester of the present invention, wherein a molar equivalent ratio of a dicarboxylic acid derivative (terephthaloyl dichloride) to a monocarboxylic acid derivative (acetic anhydride) is 10%.

2,4,4-Trimethyl-2-(2,4-dihydroxyphenyl)-7-hydroxychroman (150 g, 1.5 mol eq.) obtained in Synthesis Example 4 and METHYL ISOBUTHYL KETONE (866 g) are charged in a 2 liter four-necked flask equipped with a condenser, a thermometer, a stirrer and a dropping funnel, and then dissolved by heating to 50° C. After charging terephthaloyl dichloride (15.2 g, 0.15 mol eq.), triethylamine (15.2 g, 0.15 mol) is added dropwise over one hour. Triethylamine (151.5 g, 1.5 mol) is charged and, after heating to 70° C., acetic anhydride (153.0 g, 1.5 mol eq.) is added dropwise. After heating to 90° C. and maintaining for 5 hours, a salt was removed by washing with water and the solvent was removed under reduced pressure to obtain 212.1 g of a resinous solid having a softening point of 89° C.

According to the same manner as that described in Example 1. it was confirmed that the resultant is a desired product.

EXAMPLE 5

This Example relates to a method of producing the ester of the present invention, wherein a molar equivalent ratio of a dicarboxylic acid derivative (isophthaloyl dichloride) to a monocarboxylic acid derivative (acetic anhydride) is 30%.

2,4,4-Trimethyl-2-(2,4-dihydroxyphenyl)-7-hydroxychroman (70 g, 0.7 mol eq.) obtained in Synthesis Example 4, triethylamine (77.8 g, 0.77 mol eq.) and methyl isobutyl ketone (189.0 g) are charged in a 2 liter four-necked flask equipped with a condenser, a thermometer and a dropping funnel, followed by heating to 70° C. After adding dropwise a slurry solution prepared by dissolving isophthaloyl dichloride (21.3 g, 0.21 mol eq.) in 190.0 g of METHYL ISOBUTHYL KETONE, acetic anhydride (57.1 g, 0.56 mol eq.) is added dropwise over one hour. After heating to 90° C. and maintaining for 5 hours, a salt was removed by washing with water and the solvent was removed under reduced pressure to obtain 73.2 g of a resinous solid having a softening point of 91° C.

Infrared absorption spectrum: 2970, 1765 (carbonyl stretching of acetate), 1740 (shoulder) (carbonyl stretching of isophthalate), 1610, 1585, 1495, 1420, 1375, 1300, 1210, 1145, 1125, 1055, 1015, 900, 755 cm−1

Absorption due to OH stretching vibration was not observed.

EXAMPLE 6

This Example relates to a method of producing the ester of the present invention, wherein a molar equivalent ratio of a dicarboxylic acid derivative (dichloride adipoyl dichloride) to a monocarboxylic acid derivative (acetic anhydride) is 30%.

2,4,4-Trimethyl-2-(2,4-dihydroxyphenyl)-7-hydroxychroman (100 g, 1.0 mol eq.) obtained in Synthesis Example 4, triethylamine (77.8 g, 0.77 mol eq.) and METHYL ISOBUTHYL KETONE (600 g) are charged in a 2 liter four-necked flask equipped with a condenser, a thermometer, a stirrer and a dropping funnel, and then dissolved by heating to 40° C. After charging adipoyl dichloride (27.5 g, 0.3 mol eq.), triethylamine (30.3 g, 0.3 mol) is added dropwise over one hour. Triethylamine (80.8 g, 0.8 mol) is charged and, after heating to 60° C., acetic anhydride (81.6 g, 0.8 mol eq.) is added dropwise over one hour. After heating to 90° C. and maintaining for 4 hours, a salt was removed by washing with water and the solvent was removed under reduced pressure to obtain 144.6 g of a resinous solid having a softening point of 88° C.

Infrared absorption spectrum: 2960, 1765 (carbonyl stretching of acetate and adipate), 1610, 1580, 1495, 1370, 1200, 1140, 1120, 1055, 1010, 900, 735 cm−1

Absorption due to OH stretching vibration was not observed.

REFERENTIAL EXAMPLE 1

This Example relates to synthesis of a compound using no organic polyacid, which is essential for synthesis of the ester compound of the present invention.

2,4,4-Trimethyl-2-(2,4-dihydroxyphenyl)-7-hydroxychroman (100 g, 1.00 mol eq.) obtained in Synthesis Example 4, triethylamine (106.1 g, 1.05 mol) and methyl isobutyl ketone (568.0 g) were charged in a 2 liter four-necked round bottom flask equipped with a thermometer, a stirrer, a condenser and a dropping funnel, followed by heating to 70° C. Acetic anhydride (107.1 g, 1.05 mol) was added dropwise over 2 hours. After maintaining at 70° C. for 4 hours, the reaction solution was washed with water and partitioned to remove the aqueous layer. Then, the solvent was distilled off at 150° C. under reduced pressure of less than 5 mmHg to obtain 139.6 g of a resinous product. The resinous product was gradually crystallized when it is allowed to stand.

It was confirmed by the following analytic value that the resultant is a desired product.

Analytical value

Infrared spectrophotometry (KBr disk method)/2970, 1760 (C=0), 1605, 1580, 1490, 1420, 1200, 1145, 1125, 1100, 1035, 1010, 990, 900 cm−1

Proton nuclear magnetic resonance spectrum (solvent CDCl3)/δ (ppm) 0.79 (s, 3H, methyl), 1.30 (s, 3H, methyl), 1.64 (s, 3H, methyl), 2.13 (d, 1H, methylene), 2.24 (s, 3H, acetyl), 2.29 (s, 3H, acetyl), 2.35 (s, 3H, acetyl), 2.53 (d, 1H, methylene), 6.62–7.46 (m, 6H, aryl)

EXAMPLES 7 TO 30

Glycidyl ether of o-cresol novolak (trade name: ESCN-195 manufactured by Sumitomo Chemical Co., Ltd., epoxy equivalent: 195 g/eq.) and epoxy resins obtained in Synthesis Examples 1, 2 and 3, as the epoxy resin, the compounds obtained in Examples 1 to 6 and 2-ethyl-4-methylimidazole (trade name: Curezole 2ES4MZ, manufactured by Shikoku Kasei Kogyo Co., Ltd.) as the curing accelerator were mixed according to the proportion shown in Tables 1 to 4, and then dissolved in a solvent to form a uniform resin varnish. A resin mixture obtained from the resin varnish by distilling off the resin with heating was press-molded to obtain a resin cured board having a uniform thickness.

The dielectric constant and dielectric dissipation factor at 1 GHz of the resin cured plate, cured sample whose both surfaces are polished, were measured using an impedance analyser HP4291A and a dielectric measuring electrode BP 16453A (manufactured by Nippon Hewlett Packard Co.). The glass transition temperature was determined from an inflection point of a thermal expansion curve using a thermomechanical analyzer TMA-120 manufactured by Seiko Denshi Kogyo Co., Ltd. The formulation and results are shown in Tables 1 to 4.

COMPARATIVE EXAMPLES 1 TO 12

According to the same manner as that described in Examples 7 to 30, glycidyl ether of o-cresol novolak (trade name: ESCN-195 manufactured by Sumitomo Chemical Co., Ltd., epoxy equivalent: 195 g/eq.) and epoxy resins obtained in Synthesis Examples 1, 2 and 3 as the epoxy resin, the compound obtained in Referential Example 1, Tamanol 758 (trade name: Tamanol, manufactured by Arakawa Kagaku Kogyo Co., Ltd.) or dicyandiamide as the curing agent, and 2-ethyl-4 -methylimidazole (Curezole 2E4MZ) as the curing accelerator were used to produce a resin cured plate, respectively. The dielectric constant and dielectric dissipation factor at 1 GHz as well as glass transition temperature were measured. The formulation and results are shown in Tables 1 to 4.

TABLE 1

|  | Example 7 | Example 8 | Example 9 | Example 10 | Example 11 | Example 12 | Comparative example 1 | Comparative example 2 | Comparative example 2 |
|---|---|---|---|---|---|---|---|---|---|
| Sumiepoxy ESCN-195 | 20 | 20 | 20 | 20 | 20 | 20 | 20 | 63.7 | 92.5 |
| Ester of Example 1 | 14.9 | | | | | | | | |
| Ester of Example 2 | | 14.9 | | | | | | | |
| Ester of Example 3 | | | 14.7 | | | | | | |
| Ester of Example 4 | | | | 14.4 | | | | | |
| Ester of Example 5 | | | | | 14.6 | | | | |
| Ester of Example 6 | | | | | | 14.3 | | | |
| Ester of Referential Example 1 | | | | | | | 14.2 | | |
| Tamanol 758 | | | | | | | | 36.3 | |
| Dicyandiamide | | | | | | | | | 7.5 |
| Curezole 2E4MZ | 0.1 | 0.1 | 0.1 | 0.1 | 0.1 | 0.1 | 0.1 | 0.1 | 0.2 |
| Methyl ethyl ketone | 34.9 | 34.9 | 34.7 | 34.4 | 34.6 | 34.3 | 34.2 | 100 | 100 |
| Dielectric constant (1 GHz) | 3.03 | 3.02 | 3.05 | 3.04 | 3.10 | 2.94 | 3.15 | 3.38 | 3.41 |
| Dielectric dissipation factor (1 GHz) | 0.0131 | 0.0130 | 0.0128 | 0.0125 | 0.0130 | 0.0129 | 0.0114 | 0.0207 | 0.0255 |
| Glass transition temperature (° C., TMA) | 175 | 174 | 170 | 165 | 175 | 155 | 140 | 160 | 130 |

TABLE 2

|  | Example 13 | Example 14 | Example 15 | Example 16 | Example 17 | Example 18 | Comparative example 4 | Comparative example 5 | Comparative example 6 |
|---|---|---|---|---|---|---|---|---|---|
| Epoxy of Synthesis Example 1 | 25 | 25 | 25 | 25 | 25 | 25 | 25 | 25 | 25 |
| Ester of Example 1 | 14.9 | | | | | | | | |
| Ester of Example 2 | | 14.9 | | | | | | | |

TABLE 2-continued

|  | Example 13 | Example 14 | Example 15 | Example 16 | Example 17 | Example 18 | Comparative example 4 | Comparative example 5 | Comparative example 6 |
|---|---|---|---|---|---|---|---|---|---|
| Ester of Example 3 |  |  | 14.7 |  |  |  |  |  |  |
| Ester of Example 4 |  |  |  | 14.4 |  |  |  |  |  |
| Ester of Example 5 |  |  |  |  | 14.6 |  |  |  |  |
| Ester of Example 6 |  |  |  |  |  | 14.3 |  |  |  |
| Ester of Referential Example 1 |  |  |  |  |  |  | 14.2 |  |  |
| Tamanol 758 |  |  |  |  |  |  |  | 10.6 |  |
| Dicyandiamide |  |  |  |  |  |  |  |  | 1.47 |
| Curezole 2E4MZ | 0.18 | 0.18 | 0.18 | 0.18 | 0.18 | 0.18 | 0.18 | 0.13 | 0.13 |
| Methyl ethyl ketone | 35.9 | 39.9 | 39.7 | 39.4 | 39.6 | 39.3 | 39.2 | 35.6 | 26.5 |
| Dielectric constant (1 GHz) | 2.80 | 2.78 | 2.81 | 2.80 | 2.80 | 2.86 | 2.90 | 3.40 | 3.44 |
| Dielectric dissipation factor (1 GHz) | 0.0060 | 0.0055 | 0.0065 | 0.0063 | 0.0058 | 0.0066 | 0.0086 | 0.0200 | 0.0255 |
| Glass transition temperature (° C., TMA) | 164 | 165 | 160 | 156 | 165 | 145 | 133 | 142 | 141 |

TABLE 3

|  | Example 19 | Example 20 | Example 21 | Example 22 | Example 23 | Example 24 | Comparative example 7 | Comparative example 8 | Comparative example 9 |
|---|---|---|---|---|---|---|---|---|---|
| Epoxy of Synthesis Example 2 | 56.3 | 56.3 | 56.3 | 56.3 | 56.3 | 56.3 | 56.3 | 56.3 | 56.3 |
| Ester of Example 1 | 14.9 |  |  |  |  |  |  |  |  |
| Ester of Example 2 |  | 14.9 |  |  |  |  |  |  |  |
| Ester of Example 3 |  |  | 14.7 |  |  |  |  |  |  |
| Ester of Example 4 |  |  |  | 14.4 |  |  |  |  |  |
| Ester of Example 5 |  |  |  |  | 14.6 |  |  |  |  |
| Ester of Example 6 |  |  |  |  |  | 14.3 |  |  |  |
| Ester of Referential Example 1 |  |  |  |  |  |  | 14.2 |  |  |
| Tamanol 758 |  |  |  |  |  |  |  | 10.6 |  |
| Dicyandiamide |  |  |  |  |  |  |  |  | 1.47 |
| Curezole 2E4MZ | 0.28 | 0.28 | 0.28 | 0.28 | 0.28 | 0.28 | 0.28 | 0.2 | 0.2 |
| Methyl ethyl ketone | 71.2 | 71.2 | 71.0 | 70.7 | 70.9 | 70.6 | 70.5 | 65.9 | 57.8 |
| Dielectric constant (1 GHz) | 2.83 | 2.82 | 2.85 | 2.85 | 2.80 | 2.89 | 2.91 | 3.50 | 3.55 |
| Dielectric dissipation factor (1 GHz) | 0.0081 | 0.0080 | 0.0080 | 0.0079 | 0.0079 | 0.0087 | 0.0088 | 0.0245 | 0.0232 |
| Glass transition temperature (° C., TMA) | 149 | 150 | 145 | 140 | 151 | 140 | 130 | 140 | 138 |

TABLE 4

|  | Example 25 | Example 26 | Example 27 | Example 28 | Example 29 | Example 30 | Comparative example 10 | Comparative example 11 | Comparative example 12 |
|---|---|---|---|---|---|---|---|---|---|
| Epoxy of Synthesis Example 3 | 21 | 21 | 21 | 21 | 21 | 21 | 21 | 21 | 21 |
| Ester of Example 1 | 14.9 |  |  |  |  |  |  |  |  |
| Ester of Example 2 |  | 14.9 |  |  |  |  |  |  |  |
| Ester of Example 3 |  |  | 14.7 |  |  |  |  |  |  |
| Ester of Example 4 |  |  |  | 14.4 |  |  |  |  |  |
| Ester of Example 5 |  |  |  |  | 14.6 |  |  |  |  |
| Ester of Example 6 |  |  |  |  |  | 14.3 |  |  |  |
| Ester of Referential Example 1 |  |  |  |  |  |  | 14.2 |  |  |
| Tamanol 758 |  |  |  |  |  |  |  | 10.6 |  |
| Dicyandiamide |  |  |  |  |  |  |  |  | 1.47 |
| Curezole 2E4MZ | 0.11 | 0.11 | 0.11 | 0.11 | 0.11 | 0.11 | 0.11 | 0.04 | 0.04 |
| Methyl ethyl ketone | 35.9 | 35.9 | 35.7 | 35.4 | 35.6 | 35.3 | 35.2 | 31.6 | 22.5 |

TABLE 4-continued

|  | Example 25 | Example 26 | Example 27 | Example 28 | Example 29 | Example 30 | Comparative example 10 | Comparative example 11 | Comparative example 12 |
|---|---|---|---|---|---|---|---|---|---|
| Dielectric constant (1 GHz) | 3.01 | 3.00 | 3.03 | 3.04 | 3.04 | 2.98 | 3.03 | 3.44 | 3.39 |
| Dielectric dissipation factor (1 GHz) | 0.0104 | 0.0109 | 0.0110 | 0.0111 | 0.0098 | 0.0099 | 0.0100 | 0.0233 | 0.0245 |
| Glass transition temperature (° C., TMA) | 182 | 182 | 176 | 170 | 183 | 166 | 145 | 144 | 144 |

EXAMPLES 31 TO 36

According to the same manner as that described in Examples 7 to 30, DBU (1,8-diazabicyclo[5.4.0]-7-undecene) was used as the curing accelerator to produce a resin cured plate, respectively. The dielectric constant and dielectric dissipation factor at 1 GHz as well as glass transition temperature were measured. The formulation and results are shown in Table 5.

COMPARATIVE EXAMPLES 13 TO 15

According to the same manner as that described in Comparative Examples 1 to 20, DBU (1,8-diazabicyclo [5.4.0]-7-undecene) was used as the curing accelerator to produce a resin cured plate, respectively, and measurement of physical properties was conducted. The formulation and results are shown in Table 5.

An epoxy resin composition (50 g) prepared by formulating components according to the proportion described in Table 6 was dissolved in methyl ethyl ketone to form a uniform resin varnish having a resin content of 60%. A glass cloth (trade name: KS-1600S962LP, manufactured by Kanebo Co., Ltd) was impregnated with the varnish and then treated using a hot-air dryer at 160° C. for 6 minutes to obtain a prepreg. Five prepregs and copper foils (TSTO treatment, 35 μm in thickness, manufactured by Furukawa Circuit Foil Co., Ltd.) were laminated each other, followed by hot-pressing at 170° C. for 2 hours to obtain a copper-clad laminate having a thickness of 1 mm, respectively. Physical properties of the resulting copper-clad laminate are shown in Table 6.

TABLE 5

|  | Example 31 | Example 32 | Example 33 | Example 34 | Example 35 | Example 36 | Comparative example 13 | Comparative example 14 | Comparative example 15 |
|---|---|---|---|---|---|---|---|---|---|
| Suniepoxy ESCN-195 | 20 | 20 | 20 | 20 | 20 | 20 | 20 | 63.7 | 92.5 |
| Ester of Example 1 | 14.9 |  |  |  |  |  |  |  |  |
| Ester of Example 2 |  | 14.9 |  |  |  |  |  |  |  |
| Ester of Example 3 |  |  | 14.7 |  |  |  |  |  |  |
| Ester of Example 4 |  |  |  | 14.4 |  |  |  |  |  |
| Ester of Example 5 |  |  |  |  | 14.6 |  |  |  |  |
| Ester of Example 6 |  |  |  |  |  | 14.3 |  |  |  |
| Ester of Referential Example 1 |  |  |  |  |  |  | 14.2 |  |  |
| Tamanol 758 |  |  |  |  |  |  |  | 36.3 |  |
| Dicyandiamide |  |  |  |  |  |  |  |  | 7.5 |
| DBU* | 0.2 | 0.2 | 0.2 | 0.2 | 0.2 | 0.2 | 0.2 | 0.51 | 0.51 |
| Methyl ethyl ketone | 34.9 | 34.9 | 34.7 | 34.4 | 34.6 | 34.3 | 34.2 | 100.0 | 100.0 |
| Dielectric constant (1 GHz) | 3.03 | 3.02 | 3.00 | 2.95 | 3.03 | 2.99 | 2.95 | 3.38 | 3.44 |
| Dielectric dissipation factor (1 GHz) | 0.0131 | 0.0130 | 0.0128 | 0.0125 | 0.0137 | 0.0144 | 0.0115 | 0.0247 | 0.0253 |
| Glass transition temperature (° C., TMA) | 160 | 160 | 156 | 152 | 163 | 155 | 143 | 160 | 143 |

*DBU: 1,8-Diazabicyclo[5.4.0]-7-undecene

EXAMPLES 37 TO 45

This Example relates to a production example of a copper-clad laminate using the epoxy resin of the present invention.

TABLE 6

|  | Example 37 | Example 38 | Example 39 | Example 40 | Example 41 | Example 42 | Example 43 | Example 44 | Example 45 |
|---|---|---|---|---|---|---|---|---|---|
| ESCN-195 | 25.9 | 25.7 | 25.9 | 26.3 | — | — | — | — | — |
| ESB-400T | 40 | 40 | 40 | 40 | — | — | — | — | 40.4 |
| Epoxy of Synthesis Example 2 | — | — | — | — | 72.4 | 72.2 | 72.4 | 73 | — |

TABLE 6-continued

|  | Example 37 | Example 38 | Example 39 | Example 40 | Example 41 | Example 42 | Example 43 | Example 44 | Example 45 |
|---|---|---|---|---|---|---|---|---|---|
| Epoxy of Synthesis Example 3 | — | — | — | — | — | — | — | — | 26 |
| Ester of Example 2 | 34.1 | — | — | — | 27.6 | — | — | — | 33.6 |
| Ester of Example 3 | — | 34.3 | — | — | — | 27.8 | — | — | — |
| Ester of Example 5 | — | — | 34.1 | — | — | — | 27.6 | — | — |
| Ester of Example 6 | — | — | — | 33.7 | — | — | — | 27 | — |
| 2-Ethyl-4-methylimidazole | 0.26 | 0.26 | 0.26 | 0.26 | 0.43 | 0.43 | 0.43 | 0.43 | 0.26 |
| Tg |  |  |  |  |  |  |  |  |  |
| (TMA method) | 146 | 142 | 144 | 139 | 143 | 139 | 144 | 138 | 155 |
| (DMA method) | 194 | 180 | 189 | 185 | 178 | 175 | 177 | 176 | 187 |
| Copper foil peel strength (Kg/cm) | 1.84 | 1.79 | 1.45 | 1.9 | 1.55 | 1.66 | 1.54 | 1.78 | 1.43 |
| Boiling water absorption (%, 48 hours) | 0.34 | 0.42 | 0.34 | 0.39 | 0.33 | 0.37 | 0.33 | 0.35 | 0.26 |
| Dielectric constant |  |  |  |  |  |  |  |  |  |
| 1 MHz | 4.21 | 4.25 | 4.23 | 4.25 | 3.80 | 3.91 | 3.82 | 3.79 | 3.93 |
| 1 GHz | 4.15 | 4.19 | 4.17 | 4.16 | 3.86 | 3.95 | 3.88 | 3.83 | 3.95 |
| Dielectric dissipation factor |  |  |  |  |  |  |  |  |  |
| 1 MHz | 0.008 | 0.009 | 0.008 | 0.009 | 0.004 | 0.005 | 0.005 | 0.006 | 0.008 |
| 1 GHz | 0.006 | 0.007 | 0.007 | 0.006 | 0.006 | 0.006 | 0.005 | 0.005 | 0.007 |
| Content of resin (%) | 39 | 39 | 40 | 39 | 40 | 40 | 41 | 40 | 41 |

ESCN-195: Glycidyl ether of o-cresol novolak (ESCN-195, manufactured by Sumitomo Chemical Co., Ltd.)
ESB-400T: Glycidyl ether of tetrabromobisphenol A (ESB-400T, manufactured by Sumitomo Chemical Co., Ltd.)

COMPARATIVE EXAMPLES 16 TO 20

An epoxy resin composition (50 g) prepared by formulating components according to the proportion described in Table 7 was dissolved in methyl ethyl ketone to form a uniform resin varnish having a resin content of 60%. This resin varnish was polymerized by stirring with heating at 90° C. for 2 hours. A glass cloth (trade name: KS-1600S962LP, manufactured by Kanebo Co., Ltd) was impregnated with the varnish and then treated using a hot-air dryer at 160° C. for 6 minutes to obtain a prepreg. Five prepregs and copper foils (TSTO treatment, 35 µm in thickness, manufactured by Furukawa Circuit Foil Co., Ltd.) were laminated each other, followed by hot-pressing at 170° C. for 2 hours to obtain a copper-clad laminate having a thickness of 1 mm, respectively. Physical properties of the resulting copper-clad laminate are shown in Table 7.

TABLE 7

|  | Comparative example 16 | Comparative example 17 | Comparative example 18 | Comparative example 19 | Comparative example 20 |
|---|---|---|---|---|---|
| ESCN-195 | 10 | 31.9 | 26.4 | — | — |
| ESB-400T | — | 40.4 | 40.4 | — | — |
| Epoxy of Synthesis Example 2 | — | — | — | 84 | 79.7 |
| ESB-500 | 90 | — | — | — | — |
| Ester of Referential Example 1 | — | 27.7 | — | 16 | — |
| Tamanol 758 | — | — | 33.2 | — | 20.3 |
| Dicyandiamide | 2.3 | — | — | — | — |
| 2-Ethyl-4- | 0.1 | 0.14 | 0.33 | 0.12 | 0.28 |

TABLE 7-continued

|  | Comparative example 16 | Comparative example 17 | Comparative example 18 | Comparative example 19 | Comparative example 20 |
|---|---|---|---|---|---|
| methylimidazole |  |  |  |  |  |
| Tg |  |  |  |  |  |
| (TMA method) | 130 | 142 | 130 | 139 | 120 |
| (DMA method) | 145 | 159 | 153 | 155 | 144 |
| Copper foil peel strength (Kg/cm) | 1.86 | 1.66 | 1.65 | 1.45 | 1.32 |
| Boiling water absorption (%, 48 hours) | 0.98 | 0.95 | 0.39 | 0.67 | 0.22 |
| Dielectric constant |  |  |  |  |  |
| 1 MHz | 4.75 | 4.81 | 3.95 | 4.59 | 3.96 |
| 1 GHz | 4.56 | 4.69 | 3.97 | 4.57 | 3.97 |
| Dielectric dissipation factor |  |  |  |  |  |
| 1 MHz | 0.016 | 0.018 | 0.01 | 0.015 | 0.011 |
| 1 GHz | 0.024 | 0.022 | 0.009 | 0.016 | 0.01 |
| Content of resin (%) | 40 | 40 | 40 | 39 | 40 |

ESCN-195: Glycidyl ether of a resol novolak (ESCN-195, manufactured by Sumitomo Chemical Co., Ltd.)
ESB-400T: Glycidyl ether of tetrabromobisphenol A (ESB-400T, manufactured by Sumitomo Chemical Co., Ltd.) Terminal epoxy resin (Sumiepoxy ESB-500, manufactured by Sumitomo Chemical Co., Ltd.)

TABLE 7-continued

|  | Comparative example 16 | Comparative example 17 | Comparative example 18 | Comparative example 19 | Comparative example 20 |
|---|---|---|---|---|---|

ESB-500: Terminal epoxy resin (Sumiepoxy ESB-500, manufactured by Sumitomo Chemical Co., Ltd.) obtained by the addition reaction between diglycidyl ether of bisphenol A and tetrabromobiophenol A
Tamanol 758: Phenol novolak (Tamanol 758, manufactured by Arakawa Kagaku Kogyo Co., Ltd.)

In Tables 6 and 7, physical properties were measured in the following manner.

Glass transition temperature: It was measured from an inflection point of a thermal expansion curve using a thermomechanical analyzer TMA-120 manufactured by Seiko Denshi Kogyo Co., Ltd.

Dielectric constant, dielectric dissipation factor: They were measured using an impedance analyzer HP4291A and a derivative measuring electrode HP 16453A manufactured by Nippon Hewlett Packard Co.

Water absorption: It was calculated from a change in weight after immersing a sample in boiling water for 48 hours.

Copper foil peel strength was measured according to JIS-C-6841.

EXAMPLES 46 TO 47

Glycidyl ether of o-cresol novolak (trade name: ESCN-195 manufactured by Sumitomo Chemical Co., Ltd., epoxy equivalent: 195 g/eq.) as the epoxy resin, esters obtained in Examples 3 and 4 as the curing agent, DBU (1,8-diazabicyclo[5.4.0]-7-undecene), fumed silica FB-74 and FS-891 (both of which are manufactured by Denkikagaku Kogyo Co., Ltd.) as the filler, carnauba wax as the releasing agent and a coupling agent (trade name: SH-6040, manufactured by Toray Dow Corning Co., Ltd.) were mixed in the amount shown in Table 8 and kneaded with heating using a roll, followed by transfer molding.

Furthermore, the mixture was post-cured in an oven at 180° C. for 5 hours to obtain a cured molded article, respectively. Physical properties of this cured molded article were measured. The results are shown in Table 8.

COMPARATIVE EXAMPLES 21 TO 22

According to the same manner as that described Examples 46 to 47, glycidyl ether of o-cresol novolak (trade name: ESCN-195 manufactured by Sumitomo Chemical Co., Ltd., epoxy equivalent: 195 g/eq.) as the epoxy resin, phenol novolak Tamanol 758 (trade name: Tamanol 758, manufactured by Arakawa Kagaku Kogyo Co., Ltd.) as the curing agent, DBU (1,8-diazabicyclo[5.4.0]-7-undecene) as the curing acceleration agent, fumed silica FB-74 and FS-891 (both of which are manufactured by Denkikagaku Kogyo Co., Ltd.) as the filler, carnauba wax as the releasing agent and a coupling agent (trade name: SH-6040, manufactured by Toray Dow Corning Co., Ltd.) were mixed in the amount shown in Table 8 to obtain a cured molded article, respectively. Physical properties of this cured molded article were measured. The results are shown in Table 8.

TABLE 8

| Formulation | Example 46 | Example 47 | Comparative example 21 | Comparative example 22 |
|---|---|---|---|---|
| ESCN-195LO | 100 | 100 | 100 | 100 |
| Ester of Example 3 | 75.2 |  |  |  |
| Ester of Example 4 |  | 74 |  |  |
| Tamanol 758 |  |  | 54.4 | 54.4 |
| Spherical silica (FB-74) | 560.6 | 556.8 | 494 | 494 |
| Crushed silica (FS-891) | 140.1 | 139.2 | 123.5 | 123.5 |
| TPP |  |  |  | 1.5 |
| DBU | 2 | 2 | 2 |  |
| SH-6040 | 2 | 2 | 2 | 2 |
| Carnauba wax | 1.5 | 1.5 | 1.5 | 1.5 |
| Glass transition temperature (° C., TMA) | 155 | 153 | 148 | 149 |
| Water absorption @85%/85° C. RH 72 h | 0.18 | 0.20 | 0.31 | 0.25 |
| Package crack resistance @240° C./30 sec. 72 h | 2/8 | 2/8 | 8/8 | 8/8 |

In Table 8, an evaluation method of the cured molded article is as follows.

Glass transition temperature: It was measured from an inflection point of a thermal expansion curve using a thermomechanical analyzer TMA-120 manufactured by Seiko Denshi Kogyo.

Water absorption: It was calculated from a change in weight after maintaining under the condition of 85° C./85% RH for 72 hours, using a thermo-hygrostat (AGX-326, manufactured by Advantic Toyo Co., Ltd.).

Solder crack resistance: Test IC's (52 pin QPD package, thickness of package: 2.05 mm) were allowed to absorb water under the condition of 85° C./85% RH for 72 hours and, immediately after that, they were immersed in a solder bath at 240° C. for 30 seconds. The number of the IC's wherein a crack was formed was determined. The number of test samples: 8

The ester compound of the present invention thus obtained, as a curing agent of the epoxy resin, affords a cured article having low dielectric, low moisture absorption and high heat resistance in comparison with a conventional one. These compositions are particularly suitable as a resin for multi-layer printed circuit board and a resin for sealing semiconductor, which are used for high-speed operation or high-frequency communication.

What is claimed is:
1. An ester compound prepared by
    esterifying at least one OH group of a polyhydric phenol which is a condensation product of
        a non-substituted or substituted resorcinol represented by the following general formula (1):

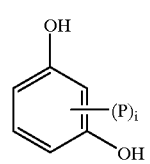

(1)

wherein P independently represents a halogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms; and i represents an integer of 0 to 2 and a carbonyl compound represented by the following general formula (2):

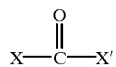

(2)

wherein X and X' independently represent a hydrogen atom, an alkyl group having 1 to 10 carbon atoms, a cycloalkyl group having 5 to 10 carbon atoms, a cycloalkyl group having 5 to 10 carbon atoms, an aryl group having 6 to 20 carbon atoms or an aralkyl group having 7 to 20 carbon atoms, and X and X' may form a ring, with an organic carboxylic acid having 1 to 20 carbon atoms or a derivative thereof, which necessarily contains an organic carboxylic polyacid having 1 to 20 carbon atoms or a derivative thereof, wherein a proportion of said organic carboxylic polyacid having 1 to 20 carbon atoms or a derivative thereof is within the range from 10 equivalent % to 50 equivalent %, based on the organic carboxylic acid having 1 to 20 carbon atoms or a derivative thereof used in the esterification.

2. The ester compound according to claim 1, wherein the polyhydric phenol as a raw material of the ester compound is a compound represented by the following general formula (3):

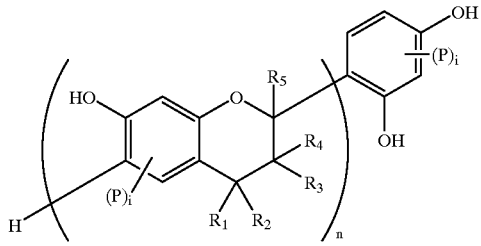

(3)

wherein n represents an average repeating number and is from 1 to 20; P independently represents a halogen atom, an alkyl group having 1 to 10 carbon atoms, an aryl group having 6 to 20 carbon atoms or an aralkyl group having 7 to 20 carbon atoms; i represents an integer of 0 to 2; and $R_1$, $R_2$, $R_3$, $R_4$ and $R_5$ independently represent a hydrogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms, and wherein $R_1$ and $R_2$ as well as $R_4$ and $R_5$ may, respectively form a ring.

3. A method for producing the ester compound of claim 1 or 2, which comprises esterifying a product, obtained by condensing the compound represented by the general formula (1) with the compound represented by the general formula (2) in the presence of an acid catalyst, with an organic carboxylic acid having 1 to 20 carbon atoms or a derivative thereof, which necessarily contains an organic carboxylic polyacid having 1 to 20 carbon atoms or a derivative thereof in the presence of a base.

4. An epoxy resin composition comprising:
(A) an epoxy resin, and
(B) the ester compound of claim 1 or 2 as an essential component.

5. A copper-clad laminate obtained from a copper foil laminated to a prepreg, said pre-preg containing a thermosetting resin in which the epoxy resin composition according to claim 4 is an essential component.

6. A copper-clad laminate according to claim 5, wherein said copper-clad laminate is obtained by thermoforming said copper foil laminated to said pre-preg.

7. An epoxy resin composition according to claim 5, wherein said epoxy resin composition comprises an inorganic filler (C), in addition to the component (A) and component (B) according to claim 4.

8. A resin-sealed semiconductor device obtained by sealing a semiconductor element with an epoxy resin composition according to claim 5.

9. A resin-sealed semiconductor device obtained by sealing a semiconductor element with an epoxy resin composition according to claim 7.

* * * * *